United States Patent
Teichert

(10) Patent No.: US 10,417,391 B2
(45) Date of Patent: Sep. 17, 2019

(54) SYSTEMS AND METHOD FOR DEVELOPING RADIATION DOSAGE CONTROL PLANS USING A PARETOFRONT (PARETO SURFACE)

(71) Applicant: Fraunhofer Gesellschaft zur Foerderung der Angewandten Forschung e.v., Munich (DE)

(72) Inventor: Katrin Teichert, Kaiserslautern (DE)

(73) Assignee: Fraunhofer-Gesellschaft zur Foerderung der angewandten Forschung e.V., Munich (DE)

( * ) Notice: Subject to any disclaimer, the term of this patent is extended or adjusted under 35 U.S.C. 154(b) by 0 days.

(21) Appl. No.: 15/261,073

(22) Filed: Sep. 9, 2016

(65) Prior Publication Data
US 2017/0242978 A1    Aug. 24, 2017

Related U.S. Application Data

(60) Provisional application No. 62/383,044, filed on Sep. 2, 2016, provisional application No. 62/298,152, filed on Feb. 22, 2016.

(51) Int. Cl.
*A61N 5/10* (2006.01)
*G06F 19/00* (2018.01)
*G16H 50/50* (2018.01)

(52) U.S. Cl.
CPC ....... *G06F 19/3481* (2013.01); *A61N 5/1031* (2013.01); *A61N 5/1047* (2013.01); *G16H 50/50* (2018.01); *A61N 5/1045* (2013.01)

(58) Field of Classification Search
CPC .......................... G06F 19/3481; A61N 5/1031
See application file for complete search history.

(56) References Cited

U.S. PATENT DOCUMENTS

| 7,391,026 B2 | 6/2008 | Trinkaus et al. |
| 8,489,366 B2 | 7/2013 | Craft et al. |
| 2013/0197878 A1* | 8/2013 | Fiege ............... A61N 5/1031 703/2 |

FOREIGN PATENT DOCUMENTS

EP   1438692 B1   12/2005

OTHER PUBLICATIONS

Pascoletti et al.; Scalarizing Vector Optimization Problems; Journal of Optimization Theory and Applications; vol. 42, No. 4, pp. 499-524; Apr. 1984; Plenum Publishing Corporation.

(Continued)

*Primary Examiner* — Thomas L Dickey
(74) *Attorney, Agent, or Firm* — Stevens & Showalter, L.L.P.

(57) ABSTRACT

System, method, and computer program product to select a desired portion of a subject to receive a radiation dose, including: determining a plurality of Pareto points on a Pareto surface (PS); selecting a first reference point ($p_1$) on a back side of an assumed Pareto surface (PS') and first direction ($q_1$) emerging therefrom towards PS' from behind; selecting a first starting adjustment ($x_{10}$) and iteratively developing forward a minimum criterion in steps until a final adjustment ($x_{11}$) is reached that still is implementable in the radiation apparatus; stopping the forward development, thereby determining $x_{11}$ represented by a final front point ($y_{11}$) as a real Pareto point of PS'; and along $q_{11}$, dismissing undetermined portions of the objective space in front of and behind $y_{11}$ as not containing parts of the PS, and continuing with other remaining more determined portions that are assumed to each contain a part of PS'.

9 Claims, 14 Drawing Sheets

(56) References Cited

OTHER PUBLICATIONS

D.T. Luc; Scalarization of Vector Optimization Problems; Journal of Optimization Theory and Applications; vol. 55, No. 1, pp. 85-102; Oct. 1987; Plenum Publishing Corporation.

Rajendra Solanki; Generating the Noninferior Set in Mixed Integer Biobjective Linear Programs: An Application to a Location Problem; Computers Ops. Res., vol. 18, No. 1, pp. 1-15; 1991; Pergamon Press plc.

Jahn et al.; Reference Point Approximation Method for the Solution of Bicriterial Nonlinear Optimization Problems; Journal of Optimization Theory and Applications; vol. 74, No. 1, pp. 87-103; Jul. 1992; Plenum Publishing Corporation.

Siegfried Helbig; On a Constructive Approximation of the Efficient Outcomes in Bicriterion Vector Optimization; Journal of Global Optimization 5, pp. 35-48; 1994; Kluwer Academic Publishers.

Solanki et al.; Approximating the noninferior set in multiobjective linear programming problems; European Journal of Operational Research 68, pp. 356-373; 1993; Elsevier Science Publishers B.V.

Benson et al.; Towards Finding Global Representations of the Efficient Set in Multiple Objective Mathematical Programming; Naval Research Logistics, vol. 44, pp. 47-67; 1997; John Wiley & Sons, Inc.

Papadimitriou et al.; On the Approximability of Trade-offs and Optimal Access of Web Sources; Foundations of Computer Science—Proceedings of the 41st Annual Symposium; Nov. 2000; IEEE Computer Society Washington, DC, USA.

Serpil Sayin; Measuring the quality of discrete representations of efficient sets in multiple objective mathematical programming; Mathematical Programming, Ser. A 87, pp. 543-560; 2000; Springer Science and Business Media.

Klamroth et al.; Unbiased Approximation in Multicriteria Optimization; Mathematical Methods of Operations Research, vol. 56, Issue 3, pp. 413-437; Jan. 2003; Springer International Publishing.

Schandl et al.; Norm-Based Approximation in Multicriteria Programming; Computers and Mathematics with Applications 44, pp. 925-942; 2002; Elsevier Science Ltd.

Kufer et al; Intensity-modulated radiotherapy—a large scale multicriteria programming problem; OR Spectrum 25;, pp. 223-249; 2003; Springer-Verlag.

Ruzika et al.; Approximation Methods in Multiobjective Programming; Journal of Optimization Theory and Applications, vol. 126, No. 3, pp. 473-501; Sep. 2005; Springer Science + Business Media, Inc.

Gabriele Eichfelder; Scalarizations for adaptively solving multiobjective optimization problems; Computational Optimization and Applications, pp. 1-21; Nov. 2009.

Kostreva et al.; A method for approximating solutions of multicriterial nonlinear Optimization problems; Optimization Methods and Software, vol. 5, pp. 209-226; 1995; Overseas Publishers Association.

H. Reuter; An approximation method for the efficiency set of multiobjective programming problems; Optimization, vol. 21, pp. 905-911; 1990; Akademie-Verlag Berlin.

Monz et al.; Pareto navigation—algorithmic foundation of interactive multi-criteria IMRT planning; Physics in Medicine and Biology, vol. 53, pp. 985-998; 2008; IOP Publishing.

Bringmann et al.; The Maximum Hypervolume Set Yields Near-optimal Approximation; The Genetic and Evolutionary Computation Conference '10; Jul. 7-11, 2010; Portland, OR.

Legriel et al.; Approximating the Pareto Front of Multi-Criteria Optimization Problems; downloaded from www-verimag.imag.fr/~maler/Papers/pareto.pdf on Jul. 26, 2017.

Bringmann et al.; Tight Bounds for the Approximation Ratio of the Hypervolume Indicator; downloaded from https://pdfs.semanticscholar.org/5dcd/c7a92316843c8912cd23770bd264f4cdc69a.pdf on Jul. 26, 2017.

Dutta et al.; A New Scalarization and Numerical Method for Constructing Weak Pareto Front of Mutli-objective Optimization Problems; Optimization; Aug. 2011.

Jorge Ivan Serna Hernandez; Multi-objective optimization in Mixed Integer Problems with application to the Beam Selection Optimization Problem in IMRT; Dissertation—Zugl.;Kaiserslautem, Technischen Universitat, Diss.; Dec. 16, 2011.

Katrin Teichert; A hyperboxing Pareto approximation method applied to radiofrequency ablation treatment planning; Dissertation; Fraunhofer ITWM, Kaiserslautern; 2013; Fraunhofer Verlag.

Schumann et al.; Interactive Multi-Criteria Planning for Radiofrequency Ablation; International Journal of Computer Assisted Radiology and Surgery, vol. 10, Issue 6, pp. 879-889; Jun. 2015; Springer Berlin Heidelberg.

Teichert, Katrin; Systems and Methods for Developing Radiation Dosage Control Plans Using a Paretofront (Pareto Surface); U.S. Appl. No. 15/261,134, filed Sep. 9, 2016.

\* cited by examiner

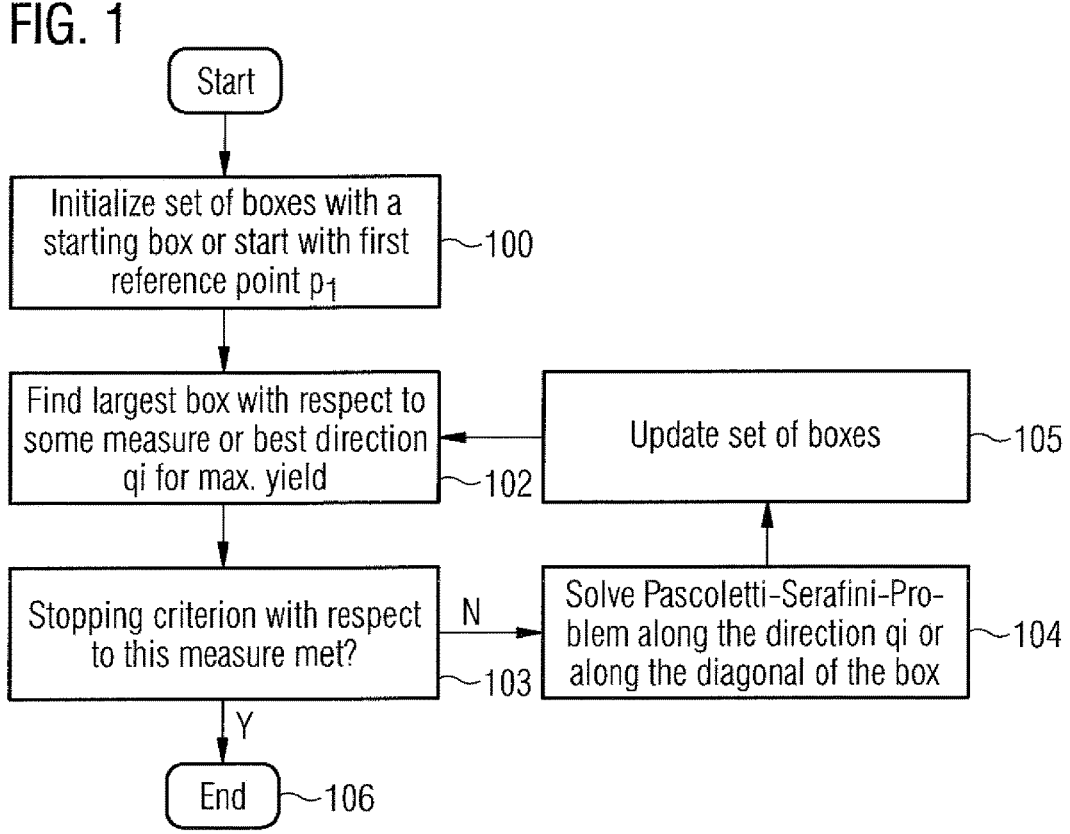

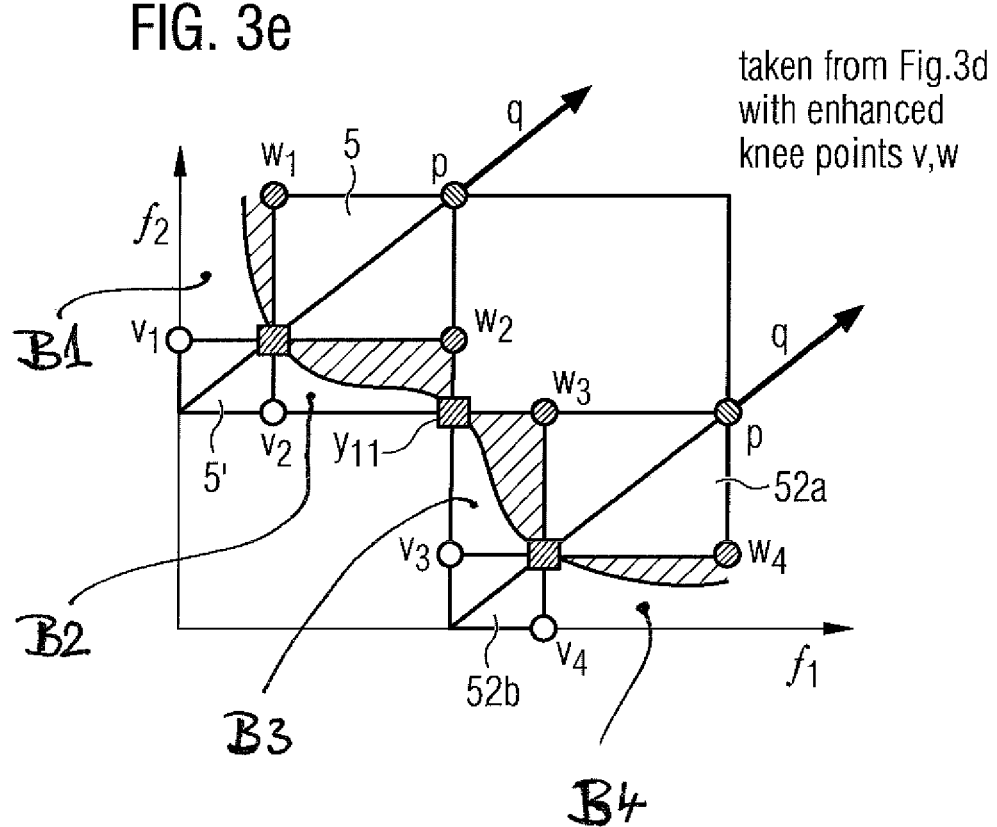

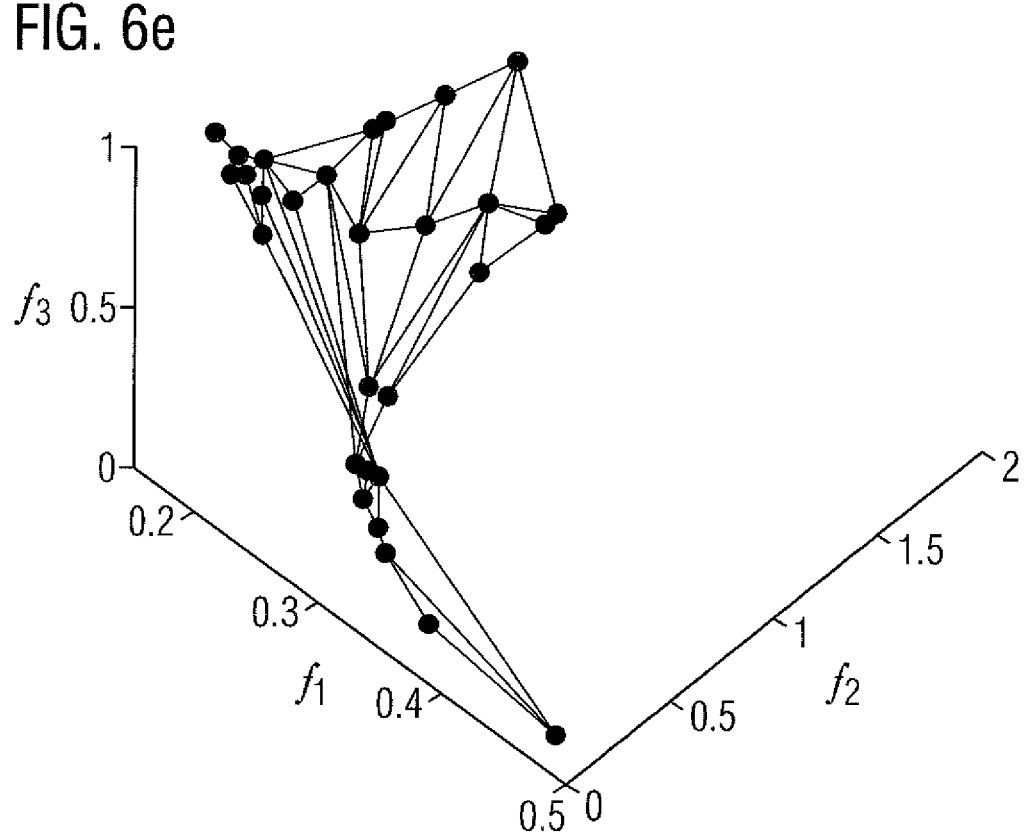

Multi core processor

SYSTEMS AND METHOD FOR DEVELOPING RADIATION DOSAGE CONTROL PLANS USING A PARETOFRONT (PARETO SURFACE)

FIELD OF THE INVENTION

This invention relates generally to program products, systems and methods for developing control plans for radiation dosage and, more particularly, to systems and methods to determine a desired plan for applying a radiation dose.

BACKGROUND OF THE INVENTION

The application of radiation to an individual is commonplace in a number of industries, such as the medical industry, where radiation is used in imaging applications and therapy applications, and the security industry, where radiation is used to perform inspection processes. Regardless of the industry, whenever radiation is applied to a living subject, a balance is sought between the ability to achieve the best results of the process utilizing the radiation, which typically leans toward increased radiation dosage, and the safety of the subject, which typically leans toward decreased radiation dosage.

The following references provide guidance: Intensity Modulated Radiotherapy: A Large Scale Multi Criteria Programming Problem, by authors Kuefer, Monz, Scherrer, Trinkaus, Bortfeld, Thieke, OR Spektrum, 2003; Unbiased Approximation in Multicriteria Optimization, by Klamroth, Tind, and Wiecek, Vol. 56 (3), 2002, pages 413 to 437 (herein Klamroth et al.); Approximation Methods in Multi-objective Programming, by Ruzika and Wiecek, Journal of Optimization Theory and Applications, Vol. 126, 2005, pages 473 to 501 (herein Ruzika et al.) and Approximating the Noninferior Set in Multiobjective Linear Programming Problems, by Solanki, European Journal of Operational Research, Vol. 68, 1993, pages 356 to 373 (herein Solanki).

U.S. Pat. No. 8,489,366 B2 (Craft and Bortfeld) discloses a method for discovering a Pareto surface but will fail when the surface has at least one concave portion (bent inwardly). It operates according to triangles that are placed around a small segment of a Pareto surface, and then iterates further steps to further define the unknown surface.

Within radiotherapy treatment planning, a search is motivated for a patient-specific best compromise between applying sufficient dose to the target and sparing organs at risk and healthy tissue. Typically, a list of clinical goals ("treatment protocol") is aspired to, containing (minimally required to optimal) target doses for specific volume quantiles of the planning structures, or reversely target quantiles for specific dose levels.

In conventional planning, (surrogate) objectives for the different aspects are weighted and combined in a single objective function, and the plan is optimized with respect to this function. However, the best weighting factors for the specific patient are not known a-priori and must be found out by the planner by trial-and-error ("human iteration loop").

Therefore it would be desirable to have a system and method that allows treatment planners and physicians to directly and systematically explore the range of treatment options with respect to the criteria given by the treatment protocol. This would allow them to understand the trade-offs for the individual patient while avoiding the time-consuming human iteration loop.

SUMMARY OF THE INVENTION

The invention overcomes the drawbacks of conventional planning ("human iteration loop"). It satisfies the need to calculate well-placed points on a Pareto surface (PS) also in the case that parts or all of the PS are non-convex, as results from the usage of non-convex objective functions or a non-convex feasible set. The invention applies the claimed method to intensity modulated radiation therapy (IMRT) and volumetric arc therapy (VMAT) problems, where it facilitates planning with respect to quantile based criteria.

The invention includes an algorithm that uses a feasible set and objective functions and this condition is satisfied by staying within a linear programming environment or within the context of convex feasible set and convex objective functions.

The invention provides for a computer program product. It further provides a method to determine or develop a previously unknown multi-dimensional surface shaped by Pareto optimal points, situated in the objective space; the Pareto optimal points define adjustments of a radiation apparatus. It further provides a method to select a desired portion of a subject to receive a desired radiation dose. Further the invention provides for several systems that select a desired portion of a subject to receive a (desired) radiation dose. Further a system as according to the invention both, configured and adapted to operate for selecting m objective functions and an initial m-dimensional starting box believed to contain a Pareto surface. Other systems and methods are disclosed as well in the other independent claims.

The Pareto Surface determines the portions of a subject (a patient) to receive a determined radiation dose.

The computer program product provides code for being executed on a computer. Preferably a multi-kernel (or multi core) computer is used. The executing code on the computer will satisfy functional tasks and requirements, such as selecting a desired portion of a subject to receive a radiation dose, by determining or developing a previously not known multi-dimensional surface. This surface is shaped by Pareto optimal points that are situated in the objective space. The Pareto points define adjustments of a given radiation apparatus, such it is not only a point but a whole set of physical or radiation parameters that give a specific setting of this radiation apparatus.

The general approach is to determine a plurality Pareto points on a Pareto surface or the other way around, the plurality of Pareto (optimal) points defines the Pareto surface. Each point however has to be determined, as it is not yet known and when known it is one item of the Pareto surface.

Therefore, the claim also mentions the assumed Pareto surface which is a surface that is not yet known but only assumed and will become more determined by each additional point that is found and defined to be a proper point of the real Pareto surface. In other terms, the assumed Pareto surface or the un-known Pareto surface will be built according to the invention into a real Pareto surface by adding up many points that span the real Pareto surface.

Reference points are used therefor and there is a development direction for each reference point that is used. Each (or at least most) specific step of the individual optimization run is commencing with step (b), continued with step (c) and resulting in step (d), where a new determined final front point is found that represents a setting of the radiation apparatus.

In step (b) a first reference point is selected, as mentioned, on a backside of an assumed Pareto surface (the assumed Pareto front). The first direction is emerging therefrom, towards the assumed Pareto surface from behind. In step (c) a first starting adjustment is provided and an iterative process is used to develop forward a minimum criterion in steps until a final adjustment is reached. Developing forward a minimum criterion is mathematically correct, although starting at $p_i$ and running towards the Pareto surface (the negative of the arrow $q_i$) from behind.

The minimum criterion can be the one from Pascoletti-Serafini, see e.g. Scalarizing vector optimization problems by Pascoletti and Serafini, Journal of Optimization Theory and Applications, Vol. 42, 1984, Issue 4, pp. 499 to 524 (herein Pascoletti-Serafini).

This final adjustment is still able to be implemented on the radiation apparatus, and thus stopping the forward development with the minimum criteria provides for a determination of the achieved final adjustment (developed from the starting adjustment of the radiation apparatus). This final adjustment is represented by the final front point for this individual optimization run (and found to be a real Pareto point of the assumed Pareto surface or Pareto front).

In step (d) along the direction towards to the front and towards to the back (in front and behind) of the achieved final front point certain portions of the objective space are dismissed. The direction just says that back and forth there is space that cannot contain any other portion that belong to the real Pareto surface. The definition of a Pareto point is that it cannot developed further forward, unless making another parameter adjustment (or setting) less suitable or worse and thus the mathematical definition says the front point must be the Pareto point. Any space towards the back of the direction is also no objective space that may or will contain parts of the Pareto surface. Therefore those spaces can be dismissed or removed or not taken further care of.

In an exemplary approach, horizontal lines or planes can be used that are building boxes in front and behind of the final front point, each box having a horizontal and vertical plane crossing in the final front point. Thus they may be removed from further consideration as volume of those boxes.

As the boxes used can be two- or more than two-dimensional, hyperboxing is used as technical term for step by step removing parts from the objective space, to finally retain the Pareto surface out of the previously full objective space. Compared to the volume, this surface is only "thin" along with a stopping criterion that determines the approximation of this surface. The smaller the stopping criterion is the thinner and precise the Pareto front is built.

Repeating steps (b) to (d) will give more and more Pareto points (PoP) from the previously unknown or previously assumed Pareto surface to build a real Pareto surface.

Having dismissed certain portions for each individual optimization run, the program or the code continues with remaining, now more determined portions that are assumed to each contain a part of the real Pareto surface presently only being an assumed Pareto surface.

In an embodiment from previously calculated points on the Pareto surface, the invention finds boxes such that the Pareto surface is contained in their union. The box dimensions provide a measure for the approximation quality realized by the previously calculated points. The box dimensions may also provide the means to determine where a new point on the PS should be calculated.

These benefits are not available in prior art approximation methods, such as the normal boundary intersection method, the epsilon constraint method, or the uniform weights scalarization approach.

These benefits are not available for a non-convex PS (non-convex objectives functions or non-convex feasible set) by means of the sandwiching method, see U.S. Pat. No. 8,489,366 (Craft and Bortfeld) mentioned previously.

In accordance with the present disclosure, a method for selecting a desired portion of a subject to receive a radiation dose is disclosed. The method includes selecting a plurality of points on a Pareto surface (PS) using a plurality of reference points and directions to identify the plurality of points, choosing additional reference points and directions to iteratively run to build up a model of the Pareto surface (or even the surface as Pareto front as such). The method further includes identifying new reference points and directions until a stopping criterion is met.

In accordance with another aspect of the present invention, a method for selecting a desired portion of a subject to receive a radiation dose is disclosed. The method includes enclosing the Pareto surface in a union of boxes and calculating box dimensions to gauge the approximation quality, and repeating the above steps until a stopping criterion (i.e. criteria) is met.

In accordance with another aspect of the invention, a system for selecting a desired portion of a subject to receive a radiation dose is disclosed. The system includes a computer having a computer program that when executed causes the computer to select a plurality of points believed to be on a Pareto surface about the desired portion of the subject using a plurality of reference points and directions to identify the plurality of points, iteratively choosing additional reference points and directions to run to build up a model of the Pareto surface. The computer is also caused to identify new reference points and directions (for a multiple kernel several in parallel) and repeat the steps until a stopping criterion is met.

In another embodiment a computer program product is disclosed, usable on a computer.

The product comprising a computer readable program code to select a desired portion of a subject to receive a radiation dose by determining or developing a previously unknown multi-dimensional surface shaped by Pareto optimal points, situated in the objective space, the Pareto optimal points defining adjustments of a given radiation apparatus, when the code is executed on the computer. The executing code is configured for . . .

a) determining a plurality of Pareto points on a Pareto surface (PS) using a plurality of reference points and development directions, emerging therefrom;

b) selecting a first reference point (named p1 as it is the first) on a back side of an assumed Pareto surface (PS') and first direction (named $q_1$ as it is the first) emerging therefrom towards the assumed Pareto surface from behind;

c) selecting a first starting adjustment and iteratively developing forward a minimum criterion in steps until a final adjustment is reached that still is implementable in the radiation apparatus; and stopping the forward development, thereby determining the achieved final adjustment represented by a final front point as a real Pareto point of the assumed Pareto surface;

d) along the first direction, dismissing undetermined portions of the objective space in front of and behind of the achieved final front point as not containing parts of the Pareto surface, and continuing with other remaining more determined portions that are assumed to each contain a part of the assumed Pareto surface.

In another embodiment a method is disclosed. The method determines or develops a previously unknown multi-dimensional surface shaped by Pareto optimal points, situated in the objective space; the Pareto optimal points define adjustments of a radiation apparatus. The method has the following steps.

Determining Pareto Points for a Pareto Surface (PS).

Select a first reference point (named p1 as it is the first point) on a back side of an assumed, not yet defined Pareto surface (PS') and selecting a first direction (named q1 as it is the first direction) emerging therefrom towards the assumed Pareto surface (PS') from behind.

Select a first starting adjustment and iteratively developing forward along the first direction a minimum criterion until a final adjustment is reached that still is implementable in the radiation apparatus; and stopping the forward development, thereby determining the achieved final adjustment represented by a final front point as a real Pareto point of the assumed Pareto surface (PS').

Dismiss undetermined portions of the objective space in front of and behind of the achieved final front point as not containing parts of the real Pareto surface.

In another embodiment a System is disclosed. The system is to select a desired portion of a subject to receive a radiation dose. The system comprises . . .

A computer and a non-transitory computer readable medium having computer readable program code thereon, the computer readable program code comprising a series of computer readable program steps to optimize, with the use of the computer, said radiation dose by steps, at least the following ones . . .

a) covering the yet un-determined Pareto surface by a set of m-dimensional boxes, the Pareto surface having a plurality of points wherein at least some points from the plurality of points are selected by solving a Pascoletti-Serafini problem along the diagonal of a box;

b) finding the largest box according to some measure;

c) comparing the measure to a threshold value;

and repeats steps a) through c) until the measure of the largest box is below the threshold value.

In still another embodiment a further System is disclosed. The system is for selecting a desired portion of a subject to receive a radiation dose, the system comprising: a computer having a computer program that when executed causes the computer to . . .

a) select a plurality of points believed to be on a Pareto surface (PS) about the desired portion of the subject using a plurality of reference points and directions, wherein at least some points from the plurality of points are selected by solving a Pascoletti-Serafini problem;

b) choose an additional reference point and a corresponding direction to run to build up an additional point of the model of the Pareto surface;

c) identify a new reference point and direction including a reference point being the upper corner and the direction being the diagonal of a m-dimensional box containing part of the Pareto surface;

and iteratively repeats steps b) and c) using the new reference point and direction for each repetition until a stopping criterion is met.

In still another embodiment a further method is disclosed. The method is for selecting a desired portion of a subject to receive a radiation dose.

A desired portion of a subject is selected, to receive a radiation dose. A computer system is provided, and with the use of the computer system, data, associated with the radiation dose, is received and the received data is processed by . . .

a) selecting surface points of a Pareto surface (PS) that defines m objective functions, and an initial m-dimensional starting box containing the points;

b) computing, from the initial box and points, a set of outer knee points and inner knee points determining a set of m-dimensional boxes whose union covers the Pareto surface;

c) increasing a number of points of the Pareto surface by adding a point in one of the boxes whose union covers the Pareto surface.

INTRODUCTION TO THE DRAWINGS

Various other features of the present invention will be made apparent from the following detailed description and the drawings relating to embodiments. They are seen to be exemplary only, not being read as limitations into the claims.

FIG. 1 shows an example of a workflow of the disclosed method.

FIG. 1a shows a radiation apparatus 60, 62 and 69, taken from U.S. Pat. No. 7,391,026.

FIG. 2 exemplifies how radiation dose affects multiple volumes of interest (VOIs). With each VOI a dose evaluating objective function $f_i$ is associated, measuring some dose average.

FIGS. 3a to 3d explain how iteratively a better approximation of a Pareto surface PS' is attained, e.g. by cutting away parts that cannot contain the Pareto surface PS. In this way a covering of the (real) Pareto surface (PS) is obtained by "boxes" (2- or 3- or multi-dimensional). The cut away boxes are 51a, 51b in FIG. 3b; 5, 5 and 52a, 52b in FIG. 3d.

FIGS. 3e to 3h further explain FIG. 3d with respect to inner knee points and outer knee points as well as their sets and the sets of boxes B1, B2, B3 and B4 that knee points define. The initial box used for starting is shown stippled in FIG. 3h (and FIGS. 3f and 3g).

FIG. 4 shows multiple reference points and directions that can be solved simultaneously. Thereby obtained points on the Pareto surface PS enable a construction of a covering set of boxes.

FIGS. 5a and 5b display Pareto surface approximations, obtained by hyperboxing . . .

FIGS. 6a to 6e are alternative Pareto surface examples of triangulated Pareto surfaces PS as developed by examples of the disclosed method. FIGS. 6a to 6e show the PS from different sides.

DETAILED DESCRIPTION OF THE EMBODIMENTS

Figure 1A:
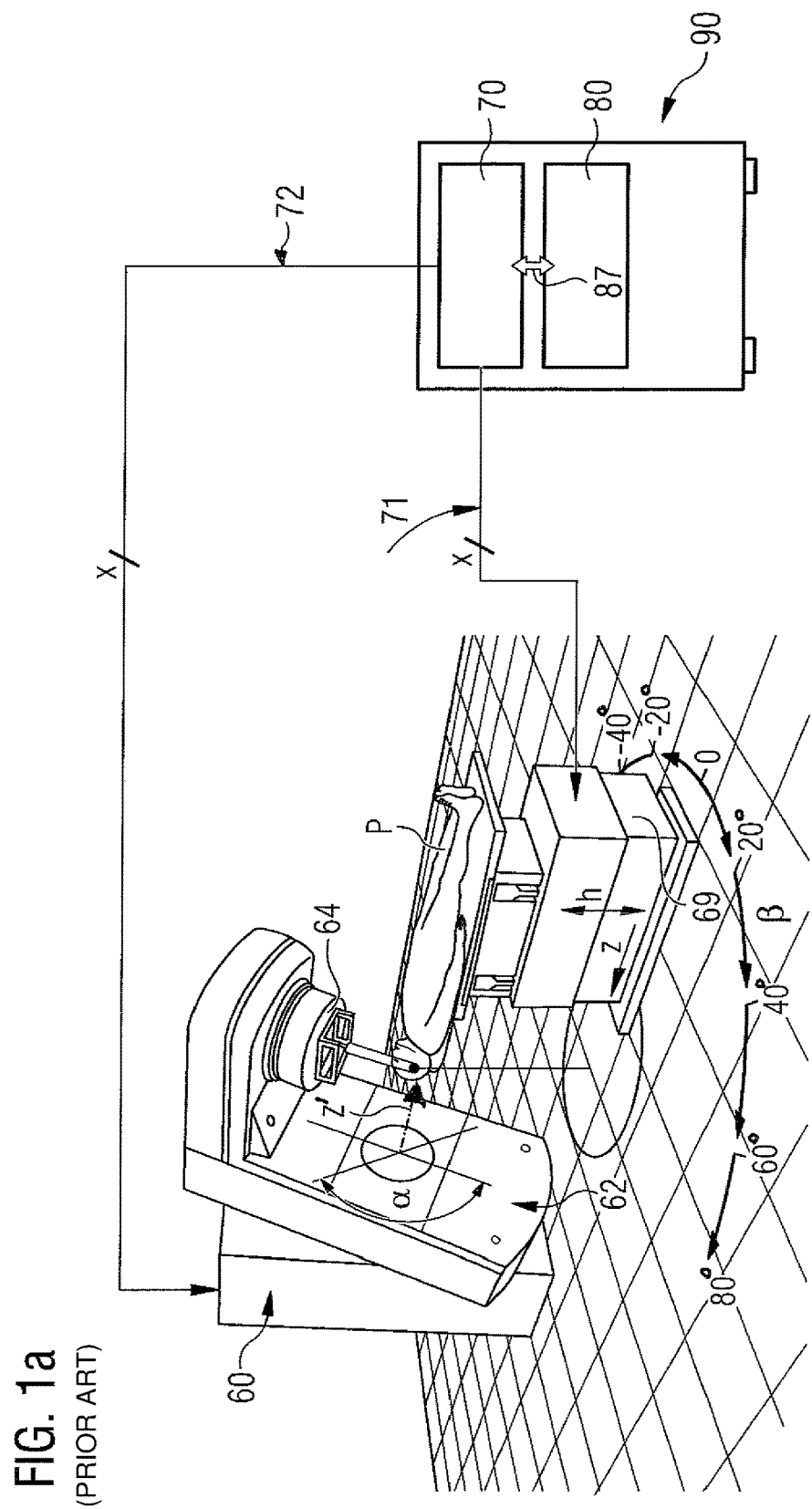

One approach is the planning problem in intensity modulated radiation therapy (IMRT) and in volumetric arc therapy (VMAT).

The radiation apparatus is not shown, as suitable ones can be found in the prior art for IMRT and VMAT therapy.

In these planning processes, a compromise between target coverage (high radiation does) and sparing (low radiation dose) of nearby critical volumes (or structures) will be found. Therefore, this constitutes an optimization problem with multiple conflicting objectives (MOP). A MOP can be represented as $$\min_{x \in X}\{f_i(x)\}, i=1,\ldots,m$$

where
x is the decision variable
X denotes the feasible set $f_i(x)$ are the objectives such that smaller values denote preferable properties of x.

In the radiation therapy context, the decision variables are the plan parameters. In particular, x may denote the fluence profile of the beam or arc fields. A description of the MOP for IMRT can be found in Kuefer et al. as to the definition of a Pareto multi-dimensional surface named "PS".

A Pareto point is a point carrying the definition of a radiation plan and being of such nature that no quality indication on the axes of the point can be improved without deteriorating a quality indication on any other of the given axes.

A plan is Pareto optimal if there is no other plan with at least equally low values for all objectives and a strictly lower value for at least one objective. The image set (or group) of the Pareto optimal points (POPs) is referred to as the Pareto surface (PS).

The examples target this MOP by computing, using a database holding Pareto optimal plans which may then be "explored" (used for evaluation of a suitable plan).

In that the invention allows the exploration of all available compromises, it differs from a range of other multi-objective optimization strategies which require specifying of the planner's preferences beforehand, such as solving weighted sum problems with fixed weights, goal programming, and lexicographic ordering.

In that the invention allows the exploration of non-convex parts of the Pareto surface, it differs from any weight-based scheme which, once or iteratively, solves weighted sum problems.

As stated above, the invention computes a database of plans on the Pareto surface (PS). This is a consequence of the fact that the PS cannot, in general, be determined in closed form. Rather, the PS must be approximated by individual points.

Based on the points computed in previous iterations, an upper and lower bound on the region where the PS is situated is provided, allowing for targeted calculation of points in places where the Pareto surface PS is not yet represented well enough.

From the representation points, a surface approximation of the Pareto surface PS can be obtained by triangulation schemes, such as the Delaunay triangulation.

Individual solutions to the multi-objective problem can be computed from scalarizations.

A most common scalarization method is the weighted sum scalarization method. However, this method does not compute solutions in non-convex parts of the PS. Thus it is not suitable to calculate a representation set in a non-convex setting, as arbitrarily large areas or parts of the Pareto surface PS are missed.

The Pascoletti-Serafini method as introduced earlier overcomes this drawback. By varying its parameters, it can obtain all Pareto optimal points on an arbitrary PS, in particular in convex and non-convex parts of a given PS alike. The Pascoletti-Serafini scalarization solves problems of the form $$\alpha \to \min$$

$$s.t. \, p + \alpha q = F(x) + \lambda$$

$$(\alpha, x, \lambda) \in \mathbb{R} \times X \times \mathbb{R}_+^m$$

Where . . .

$$F(x) = (f_1(x), f_2(x), \ldots, f_m(x))$$

is the vector of objective function values and p and q are the parameters.

For each Pareto optimal point x there is a parameter set (p,q) such that x is a solution to the corresponding Pascoletti-Serafini problem. We refer to p as the reference point and to q as the direction of the Pascoletti-Serafini problem, see FIG. 3 explaining the naming.

The fact that a non-convex Pareto surface PS or non-convex portion of a Pareto surface PS can be represented with solutions from differently parametrized Pascoletti-Serafini problems is used in the context of radiation therapy planning. There, plan quality is frequently assessed by dose and volume quantiles such as the target volume percentage receiving the prescribed dose, or the dose achieved in the target's 95% quantile. Translating these clinical goals into objectives yields non-convex functions and a non-convex PS.

The disclosure describes an iterative determination of the parameters p and q for the Pascoletti-Serafini problem such that an economic representation of an arbitrary Pareto surface is obtained. M-dimensional boxes are found and used, such that the Pareto surface PS is contained in their union. The box dimensions provide a measure for the approximation quality realized by the previously calculated points. The box dimensions also provide the means to determine where a new point on the Pareto surface PS should be calculated, and what is used as best parameters p and q to obtain that point.

Because of this usage of m-dimensional boxes, we refer to the algorithm as "hyperboxing".

The idea and concept of hyperboxing starts with an m-dimensional box containing the Pareto surface PS. In a first iteration the method solves a Pascoletti-Serafini scalarization problem "along a diagonal of the box" Thereby a minimal vertex of the box is used as the reference point p and the diagonal of the box from minimal to maximal vertex is used as direction q, see FIG. 3a.

By solving the Pascoletti-Serafini problem with the parameters p and q, a solution is found which is added to the representation set. Then the initial box is removed from the set of covering boxes, and new boxes are added to the set of covering boxes. These have been constructed from the initial box and the representation point found before.

In a following iteration the largest box from the covering boxes is chosen (by any measure, used to identify the size of a box). Within this box, the Pareto surface PS is represented most poorly so far. The Pascoletti-Serafini scalarization along the diagonal of the chosen box is solved, the solution is added as a point to the representation set, and the set of covering boxes is updated again. This iteration is repeated, until a stopping criterion (or stop criterion) with respect to a size of the largest box is met.

Figure 3A:
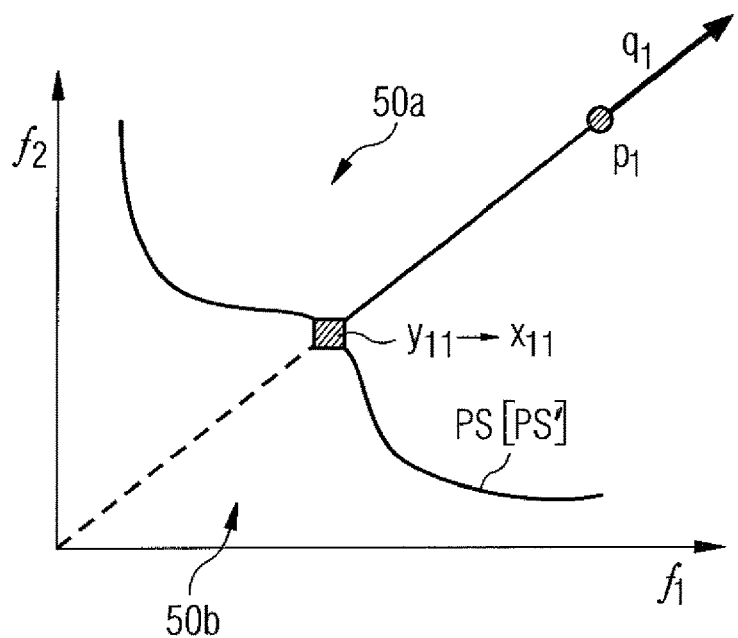
Figure 3B:
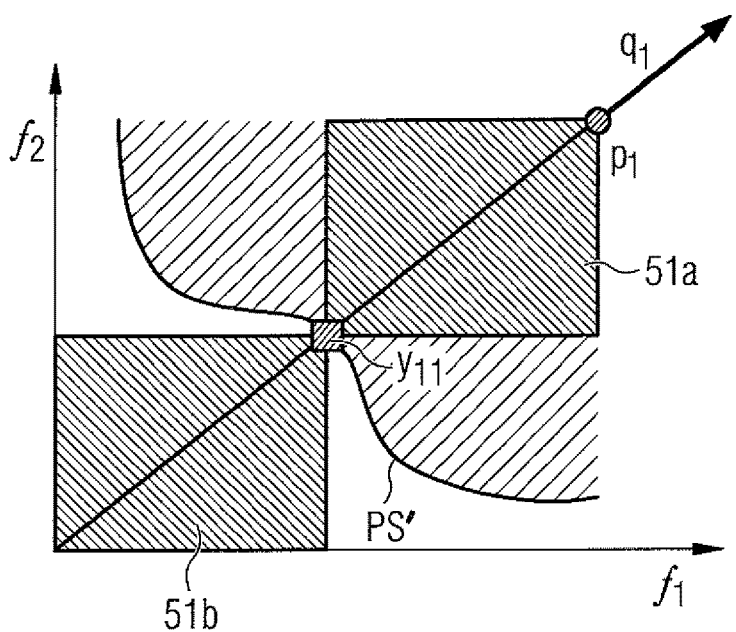

Applied to FIG. 3b, the following iteration chooses the largest box 51a from the covering boxes (by any measure, used to identify the size of a box). Within this box, the Pareto surface PS is represented most poorly so far. The Pascoletti-Serafini scalarization along the diagonal $q_1$ of the chosen box is solved, the solution is added as a point $y_{11}$ to the representation set, and the set of covering boxes is updated again. This applies in the next iteration with $y_{31}$ and $y_{21}$ in FIG. 3c, where the diagonals are $q_2$ and $q_3$. The iteration using the cut away boxes 5 and 52a is shown in FIG. 3d. Points $y_{31}$ and $y_{21}$ are added to the representation set. The set of covering boxes is then updated again.

This iteration is repeated, until a stopping criterion (or stop criterion) with respect to a size of the largest box is met.

The hyperboxing method maintains a set of boxes that, as a union, cover the Pareto surface PS. In each iteration step, larger boxes are replaced by smaller ones, strictly reducing the covered area and thus approximating the Pareto surface PS ever more tightly. This tightening is illustrated in FIG. 3, i.e., FIG. 3a to FIG. 3d, as mentioned before.

Assume having obtained $(\alpha, x_{11}, \lambda)$ as the solution of the Pascoletti-Serafini problem along the diagonal $q_1$ of an initial box, as depicted in FIG. 3a. This defines the Pareto point $y_{11}=F(x_{11})$. It holds that there are no Pareto optimal points in the area left-hand and below the point $y_{11}$ (the point marked square, not round on the diagonal q in FIG. 3b). Otherwise a lower value for $\alpha$ could have been attained in the Pascoletti-Serafini problem. The apparatus adjustment is optimized by $y=F(x)$ and its image under the evaluation criteria is a point of the real Pareto surface (PS).

Also, there are no Pareto optimal points in right-hand and above $y_{11}$ (the point marked as square on the Pareto surface PS) by definition of Pareto optimality, as shown before. Thus, the Pareto surface PS is found to be contained in the union of two remaining boxes obtained by cutting away the hatched area from the initial box, see FIG. 3b.

Figure 3C:
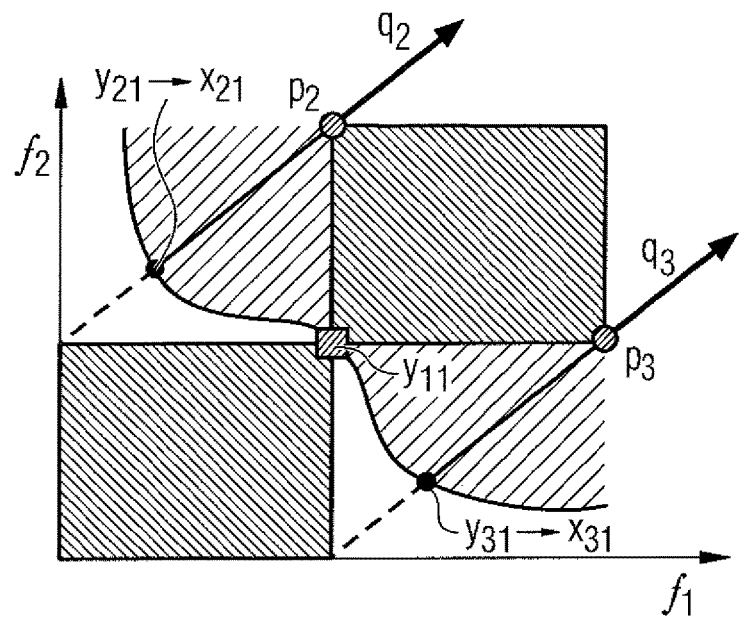
Figure 3D:
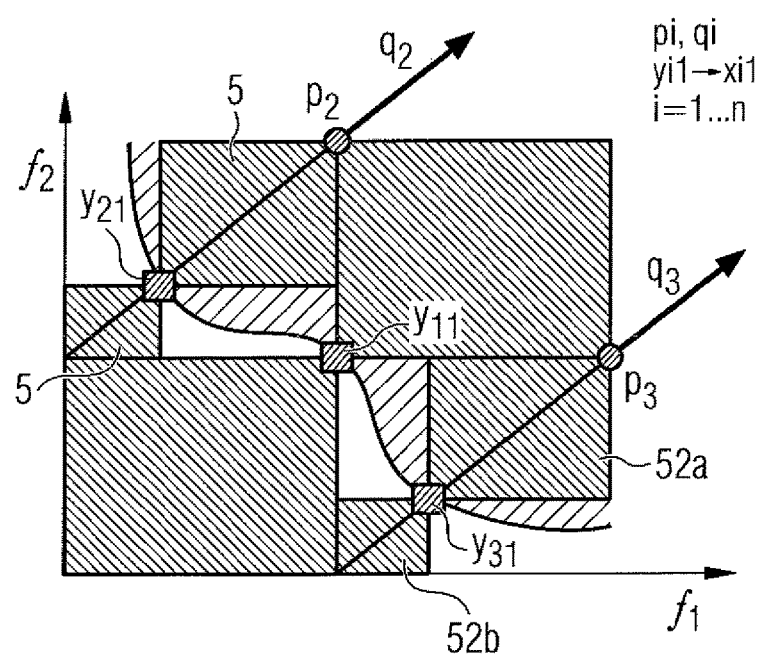

The same method step is used in the next and further iterations, leading to a set of more and smaller boxes, approximating the Pareto surface PS more tightly as shown in FIG. 3c and FIG. 3d.

Several approaches to approximate a non-convex PS have been proposed in the literature. Among those are specific algorithms to approximate the non-dominated set of a non-convex bi-criterion problem. These have never been generalized to higher dimensions, as is needed in the context of radiation treatment planning. Such generalizations to higher dimensions (as needed in the context of radiation treatment planning) are non-trivial.

Among others, generating the non-inferior set in mixed integer bi-objective linear programs: An application to a location problem, see Solanki, page 1. He considers a rectangle representation, by defining an initial rectangle containing the non-dominated set and a finite set of non-dominated points, the rectangle representation comprises the set of rectangles spanned by neighbouring points such that the non-dominated set is contained in the union of the rectangles. Each rectangle is associated with an error, namely the maximum of the rectangle sides relative to the side lengths of the initial rectangle. This prior art algorithm thus successively solves an augmented weighted Tchebycheff-Problem along the diagonal of the box with the largest error.

For higher dimensions than two, un-biased approximation in a multicriteria optimization is suggested, by Klamroth et al., page 1. This describes both, an inner and an outer approximation algorithm for the approximation non-convex non-dominated sets. The principle of splitting boxes with a weighted Tchebycheff-Method is applied here: for each of the (inner respectively outer) approximation points, an opposite point is constructed, and the lexicographic weighted Tchebycheff-Problem is solved with weights corresponding to the box dimensions. The issue there is that determining the region where the approximation is worst is a difficult disjunctive problem. As a consequence, in each iteration of the algorithm the Tchebycheff-Problems are solved for all current boxes, not for one at a time as suggested by the methods of the disclosure, called "hyperboxing".

In prior art this leads to long calculation times. The disclosure alleviates this drawback as it allows targeted refinement of the approximation on one box at a time. And using several Kernels of processors, each Kernel may calculate one box at a time, thus many boxes may still be calculated at a time, but distributed to more than one Kernel, see FIG. 7.

In contrast to the disclosure supplied herein, several other approaches of prior art do not systematically update an inner and outer approximation of the Pareto surface PS but choose each reference point and each direction a priori or randomly.

FIG. 1 shows one preferred workflow of hyperboxing. FIG. 1a shows a radiation apparatus as taken e.g. from prior art U.S. Pat. No. 7,391,026 (Fraunhofer) and its FIG. 1.

First, an initial starting box is defined at step 100. This box can be chosen such that only interesting regions of the Pareto surface PS are approximated. It can be chosen to be centred at a specifically chosen starting solution, or it can be large enough to contain the whole PS.

It may be beneficial to choose the initial starting box as small as possible, if the whole Pareto surface PS is to be contained. This will be achieved by e.g. computing the individual minima with respect to all objectives and choosing a smallest box that contains all these points as a starting box.

While it is possible that the Pareto surface PS exceeds this region, it is a reasonable estimate to start with.

Finding the true minimal starting box that contains the PS is a computational problem in dimensions greater than two.

In a next step 102, to be repeated iteratively, the "largest" box is found from the set of covering boxes. As measure for the size of a box, different metrics are possible. One possibility is to use the volume. A computationally more advantageous metric is the smallest side length of a box . . .

$$\mu(B)=\min\{L_i, i=1, \ldots, m\}.$$

Then it is checked at 103 if the measure of the largest box went below a threshold value, acting as a stop(ping) criterion. If this is the case, the method finishes at 106. Otherwise, it proceeds to step 104 with searching for an additional point on the Pareto surface PS.

To find the point, the Pascoletti-Serafini-Problem along $q_i$ of the chosen box is solved. "i" is the iteration index of loop of steps 102 to 105.

In a next step 105, the set of covering boxes may be updated. This includes removing the previously largest box, and calculating the new boxes from the old boxes and the newly found solution, as shown in FIG. 3c.

This may, for example, be achieved by updating both, the set of so-called "outer knee points" and the set of so-called "inner knee points". The outer knee points form a set of points with the following property: for each point on the Pareto surface PS there is an outer knee point that is smaller or equal in every component. Analogously, the inner knee points form a set with the following property: for each point on the Pareto surface PS there is an inner knee point that is greater or equal in every component, see J. Legriel, C. LeGuernic, S. Cotton, O. Mahler, "Approximating the Pareto Front of Multi-Criteria Optimization Problems", Tools and Algorithms for the Construction and Analysis of Systems, Lecture Notes in Computer Science, Vol. 6015/2010, pages 69 to 83, 2010 (herein Legriel et al.).

The updated set of boxes is then defined by the set of pairs comprising one inner and one outer knee point from the updated sets, respectively, such that the two points span a box with non-zero volume.

The method then proceeds to 102 again with determining the largest box from the updated set of boxes at 105.

While it is possible to alternately find a new point and update the set of covering boxes, it is also possible to simultaneously solve multiple Pascoletti-Serafini problems at 104 before updating the set of boxes again.

Figure 4:
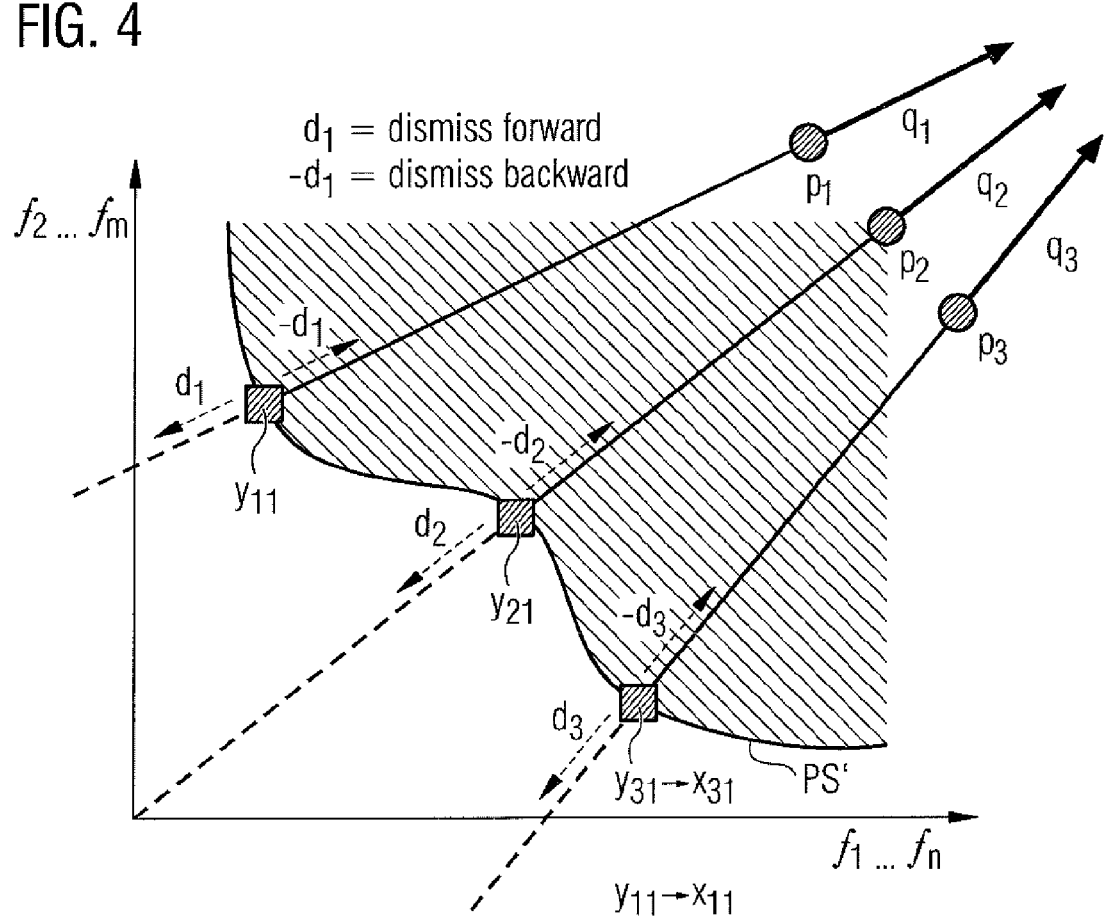
Figure 5A:
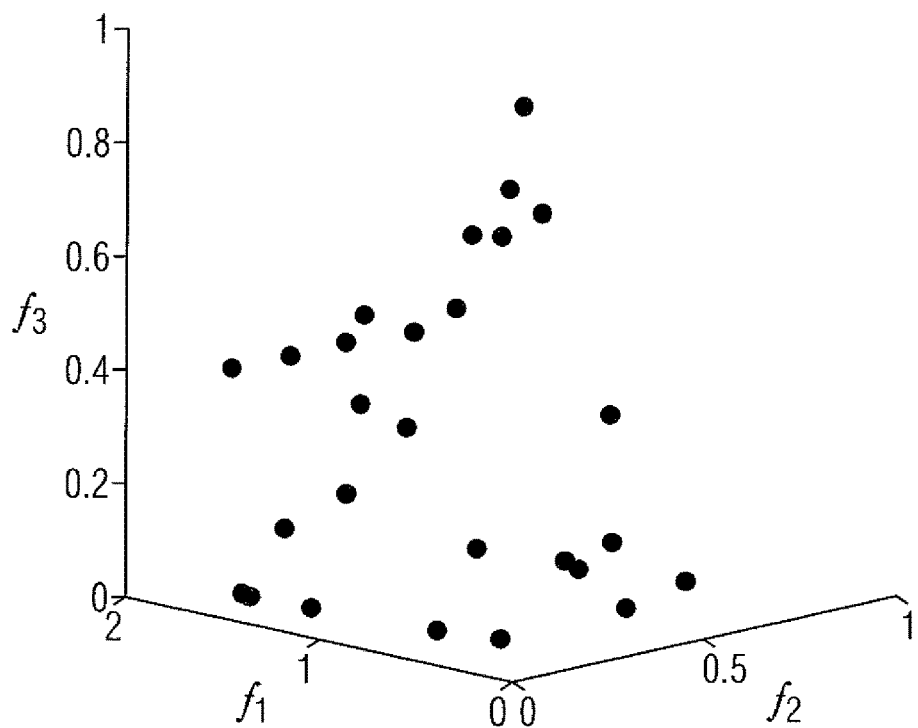
FIG. 5a shows the points with the ideal point (0,0,0) in front
Figure 5B:
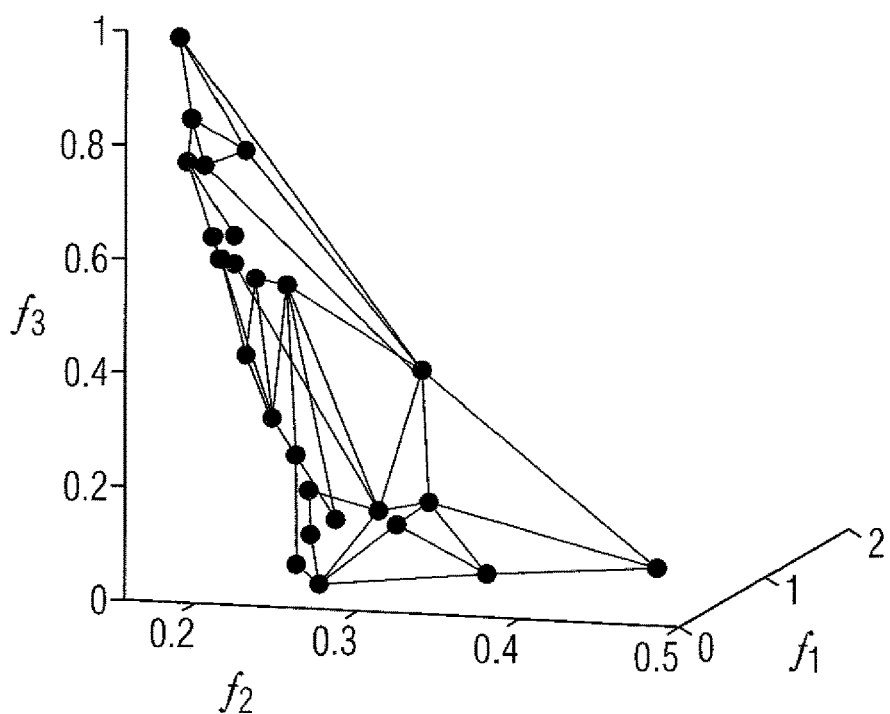
FIG. 5b shows the triangulated points seen from a side.
Figure 6A:
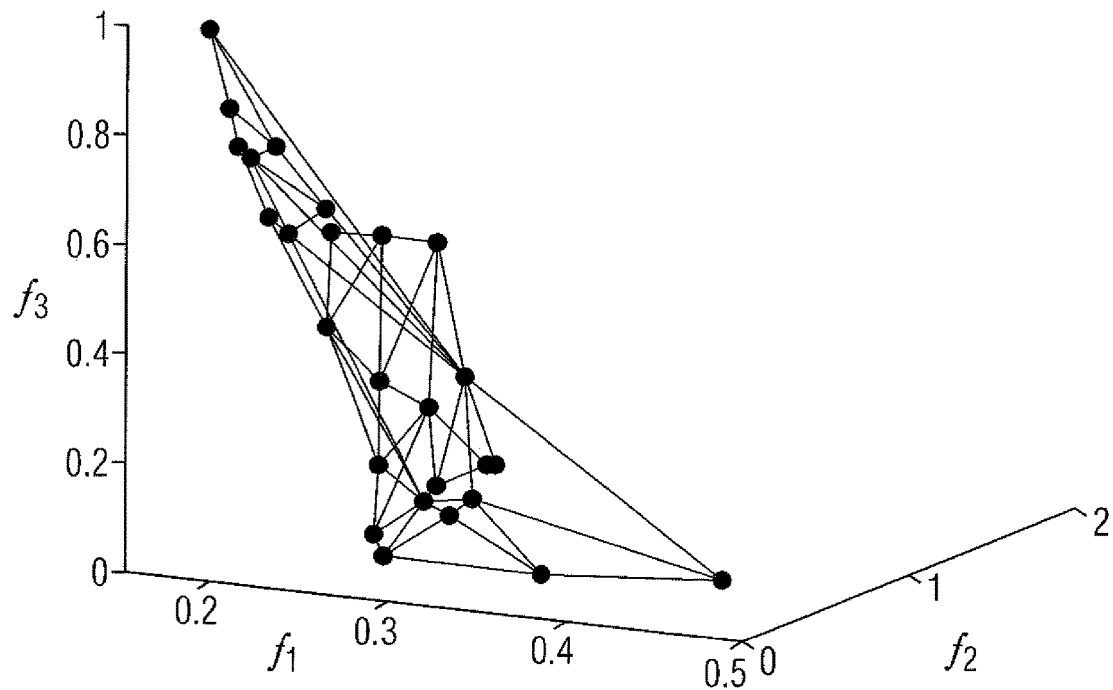
Figure 6B:
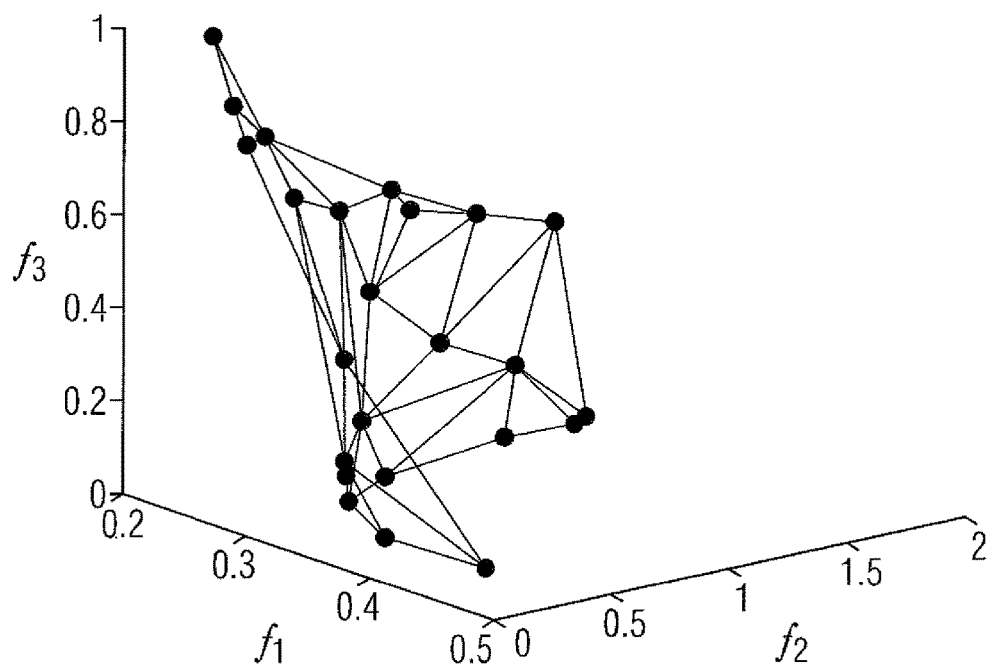
Figure 6C:
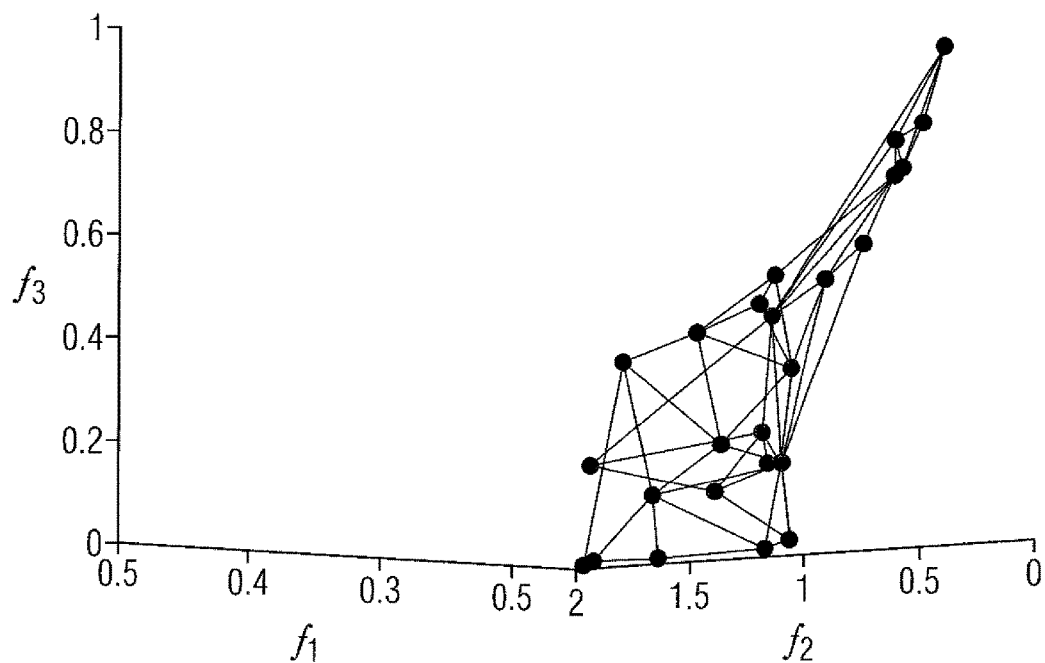
Figure 6D:
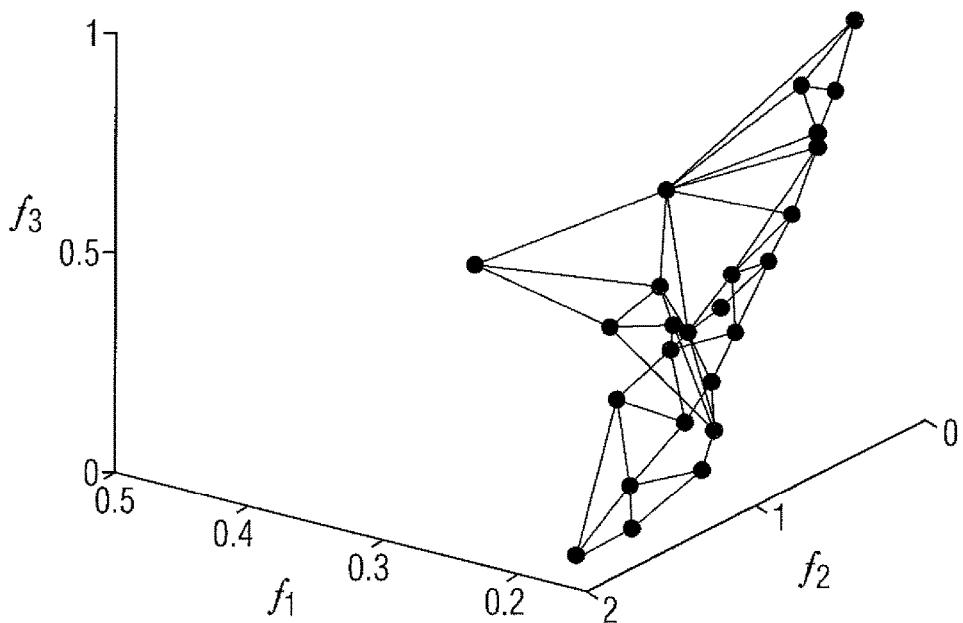

This may be done by finding new points along the diagonals of the K≥2 largest boxes within each iteration, or by varying p and/or q in some way such that multiple points are searched for simultaneously, see FIG. 4 for an example.

Figure 7:
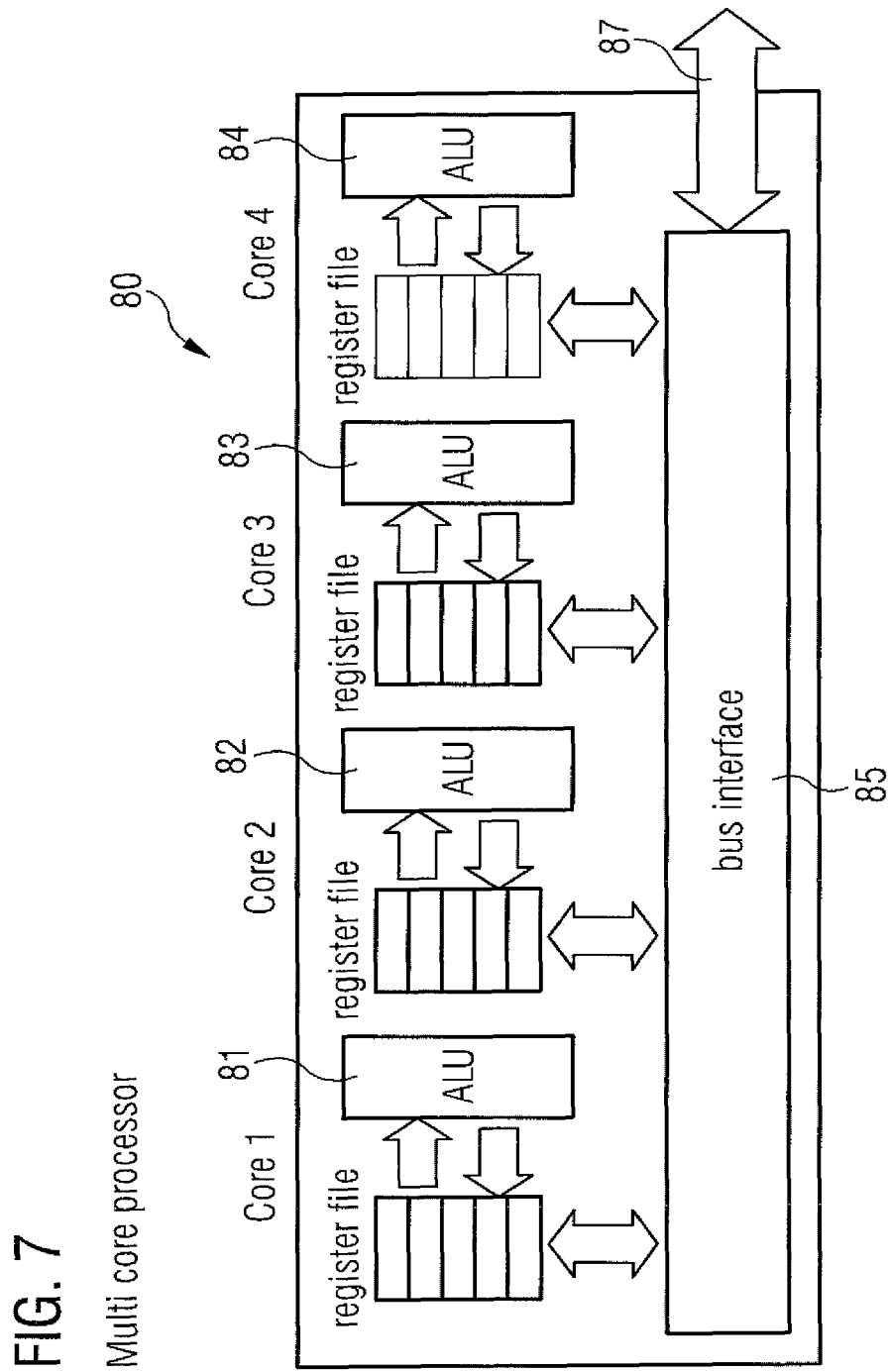
FIG. 7 shows a computer with multiple cores or kernels used in the methods disclosed herein.

This allows parallelization on a computer 80 with multiple cores (or multiple kernels) as shown in FIG. 7 and FIG. 1a. At least a few calculations along a few directions are associated with separate kernels of a multi-kernel processor 80. This multi-kernel processor 80 is depicted in FIG. 7. FIG. 7 is related to FIG. 4 that has three directions $q_1$, $q_2$, $q_3$. The multi-kernel (multi core) processor provides parallel processing. The parallel processing is exemplified in FIG. 7, where a bus interface 85 is present that has a further bus 87, coupling the bus interface to the outside of the processor. The bus interface has bidirectional connection to four kernels (cores). Each kernel (core 1, core 2, core 3 and core 4) has a register file and an ALU. This is 81 for core 1, 82 for core 2 and 83 for core 3, finally displayed is 84 for core 4. Each register file has a bidirectional link to the ALU (in and out). The register file has a bidirectional connection to the bus interface, for each of the cores 1 to 4.

Applying FIG. 4 to FIG. 7 (or vice versa), calculation along $q_1$ could be performed in core 1, calculation along $q_2$ could be performed in core 2 and calculation for direction $q_3$ could be performed in core 3. Thus at least a few calculations along a few directions $q_1$, $q_2$ and $q_3$ are associated with separate kernels of the shown multi-kernel processor 80 to provide parallel processing.

Hence, the above-described provides for calculating well-placed points on the Pareto surface PS, and applying it to the IMRT or VMAT radiation planning problem.

The method may be implemented in software that is run by a computerized system 80. A feasible set and objective functions are used and this condition is satisfied by staying within a linear programming environment or within the context of a convex feasible set and convex objective functions. Several goals are obtained, that may be combined or used individually.

The computerized system 80 is schematically shown in FIG. 1a that also shows the radiation apparatus 60, 69 as taken from prior art U.S. Pat. No. 7,391,026, a patent that is also owned by the owner of this application. In summary, FIG. 1a shows on the right hand side the computerised system in a housing 90, having the computer 80 that may be built as FIG. 7 shows. The computer 80 has a bidirectional bus 87 that connects to an interface 70 that gives control signals x to the devices 60 and 69, which are part of the full radiation apparatus. The x-parameters are plans (comprising control variables that make up each plan) and the plan controls movable elements 62, 64 and 69 of the whole radiation apparatus.

Both device parts 60 and 69 have directions to move or operate. An axis z' on the device 60 allows the turning a of device 62 with respect to a stationary part 60. The radiation beam head 64 can thus be turned along a.

The other part 69 of the radiation apparatus is not providing radiation beams, it is positioning the patient P. It can be positioned upwards and downwards along h and forward and backward along z (parallel to z'). This device may also be turned along an angle β (+80° to −40° are displayed). It receives along control line 71 signals, that make up the plan for providing the patient P with radiation doses that are as well determined by control signals x along control line 72, both emerging from interface 70. This interface receives its commands through bus 87, the commands emerge from the computerised system 80 using the PS surface.

Included in the housing 90 may also be a non-specifically displayed data base that is as well shown in the prior art radiation device of mentioned US '026 patent as database 1. The radiation apparatus 60, 62 and 69 is also explained in the corresponding European patent EP 1 438 692 B1, page 8, para [047] to [049]. Prior art radiation apparatus carries different reference signs, but has been included into this disclosure with other reference signs that more suitably match with the other reference signs used herein.

The computerized system 80 has a certain reading device to receive a computer program product, not displayed, either by inserting a readable device or system 80 is programmed by transferring the computer program product into the main memory (of the computerized system 80). The code that is transferred for the program to run is provided in this way into the computerized system 80.

Figure 2:
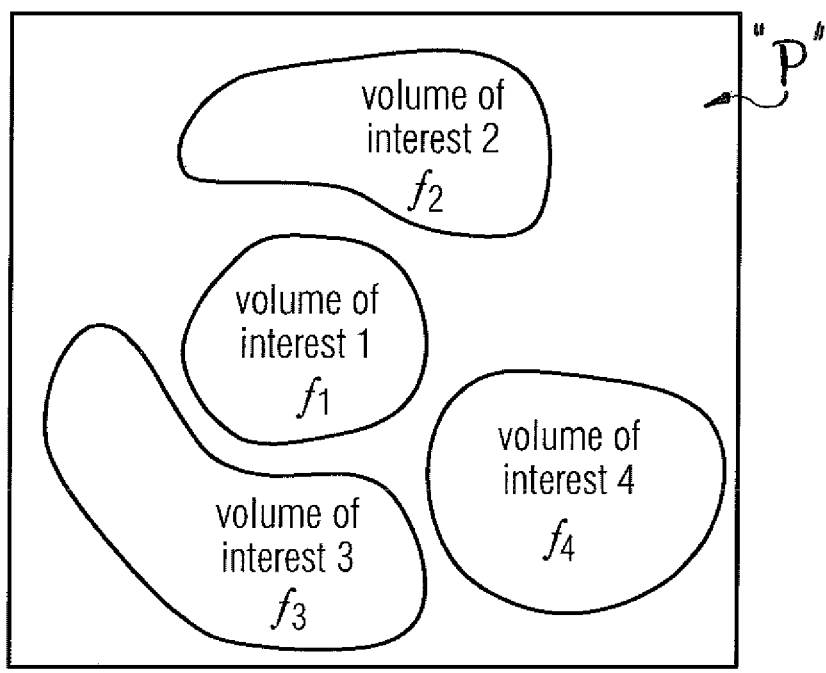

When selecting a desired portion of a subject to receive a radiation dose provided by the beam head 64 in FIG. 1a, FIG. 2 shows this abstraction of four volumes of interest 1 to 4 as can be present in the patient P. Each volume has a dose evaluating objective function $f_i$, or is associated with it, measuring a dose average for the respective volume of interest. Thus the objective function $f_1$ is related to a dose average $f_1$. The same applies for volume of interest 2 which is associated with the objective function $f_2$, measuring the dose average for volume of interest 2. The same applies for the other two abstract volumes 3 and 4 with objective functions $f_3$ and $f_4$. One of these volumes of interests may be the target, the other three ones may be the risks. Their location and distribution and size is taken from the whole body of the patient P who is to receive a treatment plan of radiation.

The hyperboxing covers the Pareto surface PS with m-dimensional boxes and iteratively approximates the Pareto surface to an arbitrary degree of exactness. The exactness may be specified by a certain size parameter that is larger or smaller, like a resolution error A when digitizing an analogue signal.

It may be specified, how to add a point to the Pareto surface PS to best improve the representation of the PS.

These benefits are not available in traditional approximation methods, such as the normal boundary intersection method, the epsilon constraint method, or the uniform weights scalarization approach. The benefits are not yet available in prior art for an at least partly or entirely non-convex Pareto surface PS, caused by non-convex objectives functions or non-convex feasible set.

For practical and computational reasons, the application may be limited to dimensions≤6 (lower than seven dimensions). The computation of the inner and outer knee points and the implicit definition of the boxes as combinations of an inner and an outer knee point may limit dimensionality in practice, as well as the computational effort to calculate a Delaunay triangulation from the Pareto points found.

In step 105 of FIG. 2, the set of covering boxes may be updated (explained earlier). This includes removing the previously largest box, and calculating the new boxes from the old boxes and the newly found solution, as shown in FIG. 3c. The same method step is used in the next and further iterations, leading to a set of more and smaller boxes, approximating the Pareto surface PS more tightly as shown in FIG. 3c and FIG. 3d.

Figure 3F:
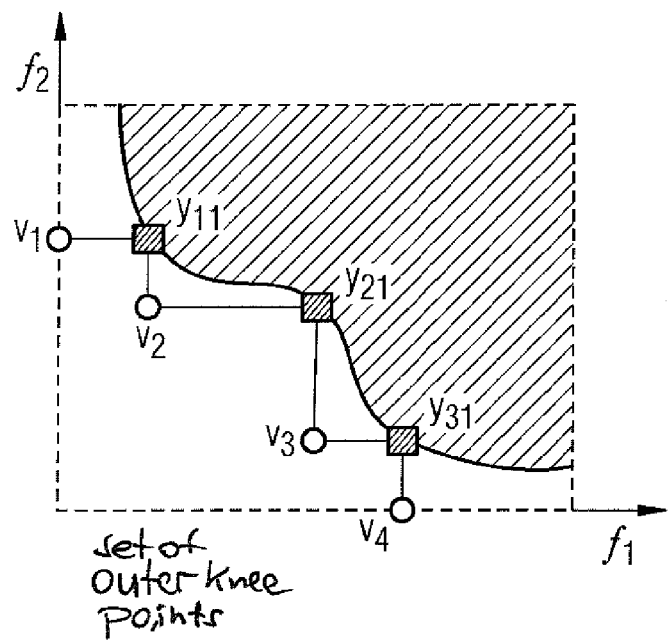
Figure 3G:
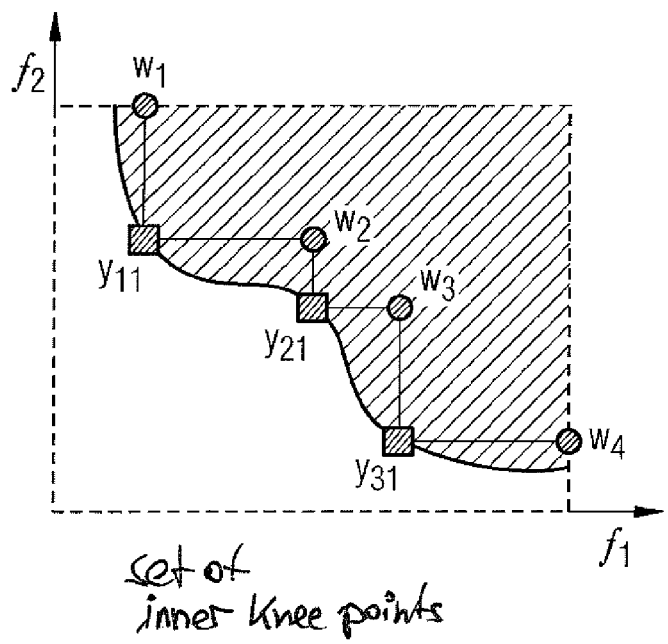

This may, for example, be achieved by updating both, the set of so-called "outer knee points" $v_i$ and the set of so-called "inner knee points" $w_i$ as present in FIG. 3d and highlighted in FIGS. 3f and 3g, both together in FIGS. 3e und 3h.

The outer knee points v of FIG. 3e form a set of points $v_1$, $v_2$, $v_3$, $v_4$, ... with the following property: for each point (e. g. $y_{11}$, $y_{21}$, $y_{31}$) on the Pareto surface PS there is an outer knee point that is smaller or equal in every component. Analogously, the inner knee points w of FIG. 3e form a set with the following property: for each point (e. g. $y_{11}$, $y_{21}$, $y_{31}$) on the Pareto surface PS there is an inner knee point that is greater or equal in every component, see Legriel et al. earlier in this disclosure.

The updated set of boxes is then defined by the set of pairs comprising one inner knee point $w_i$ and one outer knee point $v_j$ from the updated sets, respectively, such that the two points span a box with non-zero volume.

When viewing at FIG. 3e, the outer knee points v and the inner knee points w of FIG. 3d can be easily spotted. In FIG. 3e they have names, $v_j$ (j is running from 1 to 4) and $w_i$ (i is running from 1 to 4). In FIG. 3d the names of the knee points are not yet presented. In both FIG. 3e and FIG. 3h the boxes are each spanned by a pair of knee points. Namely, these are box B1, spanned by knee points $v_1$ and $w_2$ (one outer and one inner knee point), box B2 is spanned by knee points $v_2$ and $w_2$, box B3 is spanned by knee points $v_3$ and $w_3$ and box B4 is spanned by knee points $v_4$ and $w_4$. These are boxes of non-zero volume that in their entirety form a set of covering boxes that approximate the Pareto surface PS.

Now separating FIG. 3e (or FIG. 3d) will yield FIGS. 3f and 3g. FIG. 3g shows the inner knee points $w_1$, $w_2$, $w_3$, $w_4$ and their relation to a respective point on the Pareto surface. FIG. 3f shows the outer knee points $v_1$, $v_2$, $v_3$, $v_4$, also related to a respective point on the Pareto surface. The points on the Pareto surface are $y_{i1}$.

Figure 3H:
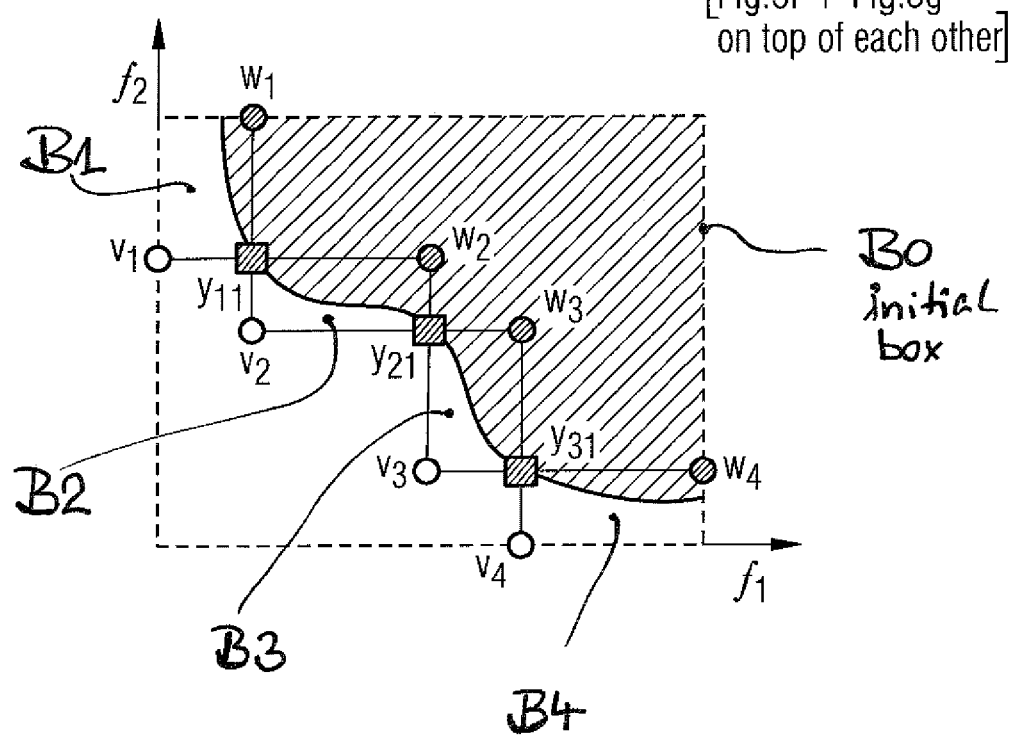

Using FIGS. 3g and 3f together and putting them on top of each other, will yield FIG. 3h, where the same structure is given as shown in FIG. 3d, outlining the boxes covering the Pareto front PS, as discussed before. This is exactly what is shown in FIG. 3d, just outlining or enhancing the points that are present in FIG. 3d already.

From FIGS. 3d, 3e it may be taken that from the initial box B0 (given by broken line in FIG. 3h) and the set of Pareto points $y_{11}$, $y_{21}$ and $y_{31}$ a set of outer knee points $v_1$, $v_2$, $v_3$, $v_4$ and a set of inner knee points $w_1$, $w_2$, $w_3$, $w_4$ may be computed.

The initial box B0 is shown in broken lines in FIG. 3h (encompassing the set of boxes B1 to B4, each made up with a pair of knee points (outer and inner knee point). Thus a set of m-dimensional boxes may be determined. The union of these boxes covers the Pareto surface (at least a portion thereof). The number of points on the Pareto surface can now be increased by adding one point in one of the B1 to B4 boxes whose union covers the Pareto surface.

Thus surface points on the Pareto surface PS define m objective functions, using the initial m-dimensional starting box containing the points.

Disclosed is a system and a method for determining a desired portion of a subject to receive a radiation dose, including iteratively updating eligible reference points and directions to gradually build up a Pareto surface. By examining the previously calculated points on the Pareto surface and the eligible reference points and directions, a next reference point and direction is chosen, to yield a new Pareto optimal point (PoP) on the Pareto surface. This iteration step is repeated until a criterion to stop is met.

The invention has been described in terms of the various aspects and features, and it should be appreciated that many equivalents, alternatives, variations, and modifications, aside from those expressly disclosed, are in the skilled man's reach (PHOSITO's reach) and thus within the scope of the invention as claimed. Therefore, the disclosure should not be limited to a particular embodiment.

What is claimed is:

1. A method to select a desired portion of a subject to receive a radiation dose by determining or developing a previously unknown multi-dimensional surface shaped by Pareto optimal points, situated in an objective space, the Pareto optimal points defining adjustments of a radiation apparatus (60,62,69), the method comprising:
   determining Pareto points for a Pareto surface (PS) by:
   a) selecting a first reference point (p1) on a back side of an assumed, not yet defined Pareto surface (PS') and selecting a first direction (q1) emerging therefrom towards the assumed Pareto surface (PS') from behind;
   b) selecting a first starting adjustment ($x_{10}$), iteratively developing forward, by solving a Pascoletti-Serafini problem, along the first direction ($q_{10}$) a minimum criterion until a final adjustment ($x_{11}$) is reached that still is implementable in the radiation apparatus (60, 62,69), and stopping the forward development, thereby determining the achieved final adjustment ($x_{11}$) represented by a final front point ($y_{11}$) as a real Pareto point of the assumed Pareto surface (PS'); and
   c) dismissing undetermined portions of the objective space in front of and behind of the achieved final front point ($y_{11}$) as not containing parts of the Pareto surface, thereby determining one or more Pareto points on or for the Pareto surface (PS) that comprises at least a portion that is non-convex;
   wherein the method further comprises developing, based on the Pareto surface, an intensity modulated radiation therapy (IMRT) or volumetric arc therapy (VMAT) treatment plan that optimizes the radiation dose for the subject, wherein the Pareto surface determines the desired portion of the subject to receive the radiation dose; and
   controlling delivery of radiation to the desired portion of the subject by adjusting, based on the IMRT or VMAT treatment plan, a position of one or more movable elements of the radiation apparatus.

2. The method of claim 1, wherein the adjustments of the radiation apparatus are optimized by y=F (x) and an image under the evaluation criterion is a point of the Pareto surface (PS).

3. The method of claim 2, wherein at least a few calculations along a few directions are associated with separate kernels of a multi kernel processor (80) to provide parallel processing.

4. The method of claim 1, further comprising repeating steps a) through c) with a next reference point ($p_2$) and a next direction ($q_2$) to a next final adjustment ($x_{21}$), represented by a next final front point ($y_{21}$) on the assumed Pareto surface (PS'), the next final adjustment still being implementable in the radiation apparatus (60,62,69).

5. The method of claim 4, further comprising:
   repeating steps a) through c) with a further reference point ($p_3$) and a further direction ($q_3$) to a further final adjustment ($x_{31}$) that still is implementable in the radiation apparatus;
   stopping the further forward development, thus determining the further final adjustment as next final adjustment ($x_{31}$), represented by a further final front point ($y_{31}$) as a Pareto point of the Pareto surface (PS); and dismissing undetermined portions of the objective space in front of and behind the further final front point ($y_{31}$) along the third direction ($q_3$).

6. The method of claim 1, further comprising repeating steps a) through c) until a stopping criterion is met, each repetition comprising:
repeating steps a) through c) with a further reference point ($p_i$), a further direction ($q_i$), and a further starting adjustment to obtain a further final adjustment ($x_{i1}$) that still is implementable in the radiation apparatus, represented by a further front point ($y_{i1}$), to yield a further final front point ($y_{i1}$) by each repetition, and gain a plurality of further final front points;
the stopping criterion being associated with an error measure of a remaining, more determined portion, determined by a length, size, or a volume thereof, to build up a determined Pareto front as multi-dimensional Pareto surface of given approximation and thus approximation quality.

7. The method of claim 1, wherein a plan is Pareto optimal if there is no other plan with at least equally low values for all objectives and a lower value for at least one objective and an image set of the Pareto optimal plans as points is the Pareto surface (PS).

8. A system for selecting a desired portion of a subject to receive a radiation dose by determining or developing a previously unknown multi-dimensional surface shaped by Pareto optimal points, situated in an objective space, the Pareto optimal points defining adjustments of a radiation apparatus (60,62,69), the system comprising:
a computer; and
a non-transitory computer readable medium having computer readable program code thereon, the computer readable program code comprising a series of computer readable program steps to determine, with the use of the computer, Pareto points for a Pareto surface (PS) by:
selecting a first reference point (p1) on a back side of an assumed, not yet defined Pareto surface (PS') and selecting a first direction (q1) emerging therefrom towards the assumed Pareto surface (PS') from behind;
selecting a first starting adjustment ($x_{10}$), iteratively developing forward, by solving a Pascoletti-Serafini problem, along the first direction ($q_{10}$) a minimum criterion until a final adjustment ($x_{11}$) is reached that still is implementable in the radiation apparatus (60,62,69), and stopping the forward development, thereby determining the achieved final adjustment ($x_{11}$) represented by a final front point ($y_{11}$) as a real Pareto point of the assumed Pareto surface (PS'); and
dismissing undetermined portions of the objective space in front of and behind of the achieved final front point ($y_{11}$) as not containing parts of the Pareto surface, thereby determining one or more Pareto points on or for the Pareto surface (PS) that comprises at least a portion that is non-convex;
wherein the series of computer readable program steps further comprises developing, based on the Pareto surface, an intensity modulated radiation therapy (IMRT) or volumetric arc therapy (VMAT) treatment plan that optimizes the radiation dose for the subject, wherein the Pareto surface determines the desired portion of the subject to receive the radiation dose; and
wherein the series of computer readable program steps further comprises controlling delivery of radiation to the desired portion of the subject by adjusting, based on the IMRT or VMAT treatment plan, a position of one or more movable elements of the radiation apparatus.

9. A system for selecting a desired portion of a subject to receive a radiation dose and controlling operation of a radiation apparatus, the system comprising:
a computer; and
a non-transitory computer readable medium having computer readable program code thereon, the computer readable program code comprising a series of computer readable program steps to optimize, with the use of the computer, the radiation dose by:
a) covering a yet un-determined Pareto surface by a set of m-dimensional boxes, the Pareto surface having a plurality of points, wherein at least some points from the plurality of points are selected by solving a Pascoletti-Serafini problem along a diagonal of one of the m-dimensional boxes, wherein the Pareto surface is for intensity modulated radiation therapy (IMRT) or volumetric arc therapy (VMAT) planning;
b) finding a largest box according to a measure;
c) comparing the measure to a threshold value;
d) updating the set of boxes;
e) repeating steps b) to d) until the measure of the largest box is below the threshold value to approximate the Pareto surface to a predetermined degree of exactness;
f) developing, based on the approximated Pareto surface, an IMRT or a VMAT treatment plan that optimizes the radiation dose for the subject, wherein the approximated Pareto surface determines the desired portion of the subject to receive the radiation dose; and
g) controlling delivery of radiation to the desired portion of the subject by adjusting, based on the IMRT or VMAT treatment plan, a position of one or more movable elements of the radiation apparatus.

* * * * *